US006479072B1

United States Patent
Morgan et al.

(10) Patent No.: US 6,479,072 B1
(45) Date of Patent: Nov. 12, 2002

(54) MICROFABRICATED MEMBRANES AND MATRICES

(75) Inventors: Jeffrey R. Morgan, Sharon; George D. Pins, Randolph, both of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/500,829

(22) Filed: Feb. 10, 2000

Related U.S. Application Data

(60) Provisional application No. 60/119,761, filed on Feb. 11, 1999.

(51) Int. Cl.[7] .......................... A61F 13/00; A61K 9/70; C12M 1/00; A01N 1/00
(52) U.S. Cl. .................... 424/443; 424/422; 435/283.1; 435/284.1
(58) Field of Search .............................. 424/93.21, 443, 424/422; 435/283.1, 284.1

(56) References Cited

U.S. PATENT DOCUMENTS

| | | | | |
|---|---|---|---|---|
| 4,829,000 A | | 5/1989 | Kleinmann et al. | 435/240 |
| 5,273,900 A | * | 12/1993 | Boyce | 435/240.23 |
| 5,489,304 A | | 2/1996 | Orgill et al. | 623/15 |
| 5,667,961 A | | 9/1997 | Bernard et al. | 435/1 |
| 5,716,411 A | | 2/1998 | Orgill et al. | 623/15 |

OTHER PUBLICATIONS

P Zuska, Managing Device and Drug Recalls, "Microtechnology Opens Doors to the Universe of Small," Jan. 1997, 1–7.*
S. Goodman et al., Biomaterials, vol. 17, No. 21, Jan. 1996, pp. 2087–2095.*
S. Boyce et al., Journal of Biomedical Materials Research, vol. 22, Oct. 1988, pp. 939–957.*
H. Jansen et al., Micro Electro Mecnaical Systems, I.E.E.E., 1995, pp. 88–93.*
S.T. Boyce et al., "Structure of a Collagen–CaG Derman Skin Substitute Optimized for Cultured Human Epiderman Keratinocytes", *J. Biomed. Mat. Res.*, vol. 22, pp. 939–957, Oct. 1988.
B.A. Dalton et al., "Modulation of Corneal Epithelial Stratification by Polymer Surface Topography", *J. Biomed. Mat. Res.*, vol. 45, pp. 384–394, Jun. 1999.
J.H. Fitton et al., "Surface Topography Can Interfere With Epithelial Tissue Migration", *J. Biomed. Mat. Res.*, vol. 42, pp. 245–257, Nov. 1998.
R.C. Flemming et al., "Effects of Synthetic Micro– and Nano–Structured Surfaces on Cell Behavior", *Biomaterials*, vol. 20, pp. 573–588, Mar. 1999.
A. Bruno Frazier et al., "Metallic Microstructures Fabricated Using Photosensitive Polyimide Electroplating Molds", *Journal of Microelectromechanical Systems*, vol. 2, No. 2, pp. 87–94, 1993.
S.L. Goodman et al., "Three–Dimensional Extracellular Matrix Textured Biomaterials", *Biomaterials*, vol. 17, pp. 2087–2095, Nov. 1996.
Sebastien Henry et at. "Microfabricated microneedles: A Novel Approach to Transdermal Drug Delivery", *Journal of Pharmaceutical Sciences®*, vol. 87, No. 8 pp. 922–925, 1998.
Henri Jansen et al., "The Black Silicon Method IV: The Fabrication of Three–Dimensional Structures in Silicon with High Aspect Ratios for Scanning Probe Microscopy and Other Applications", *J. Micro Electro–Mechanical Systems*, I.E.E.E., Piscataway, N.J. 88–93, 1995.
W. Maly, "An Introduction to VLSI Processes", *Atlas of IC Technologies—Benjamin/Cummings Publishing Company, Inc.*, pp. 1–37, 1987.
Daniel A. Medalie et al. "Evaluation of Human Skin Reconstituted from Composite Grafts of Cultured Keratinocytes and Human Acellular Dermis Transplanted to Athymic Mice", *Journal of Investigative Dermatology*, vol. 107, No. 1, pp. 121–127, 1996.
Peter Zuska "Microtechnology Opens Doors to the Universe of Small Space", *MD&DI archive*, 1997.
"An Introduction to Laser Micromachining . . . ", *Potomac–laser.com* 1999.

* cited by examiner

Primary Examiner—Deborah Crouch
Assistant Examiner—Joseph Woitach
(74) Attorney, Agent, or Firm—Fish & Richardson P.C.

(57) ABSTRACT

The invention relates to microfabricated membranes and matrices that have a highly controlled and complex three-dimensional topography. The new micro fabricated membranes and matrices can be prepared of man-made as well as natural materials, such as materials found in naturally occurring membranes, and thus can be made in the form of tissue substitutes or analogs, such as basal lamina, dermal, or skin analogs.

23 Claims, 9 Drawing Sheets

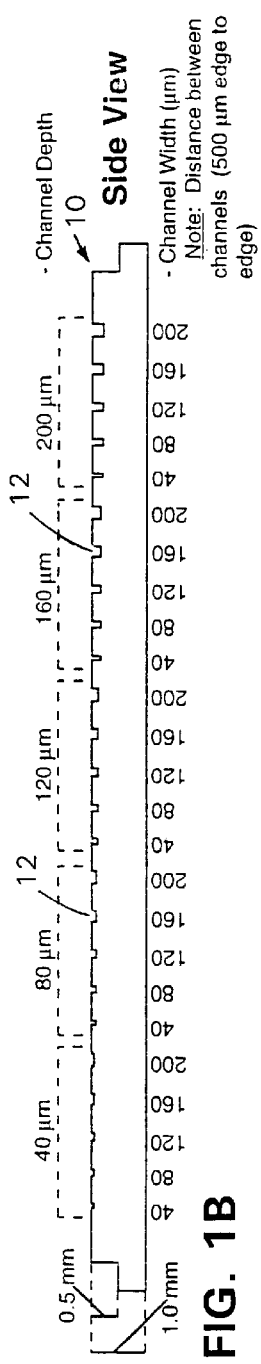
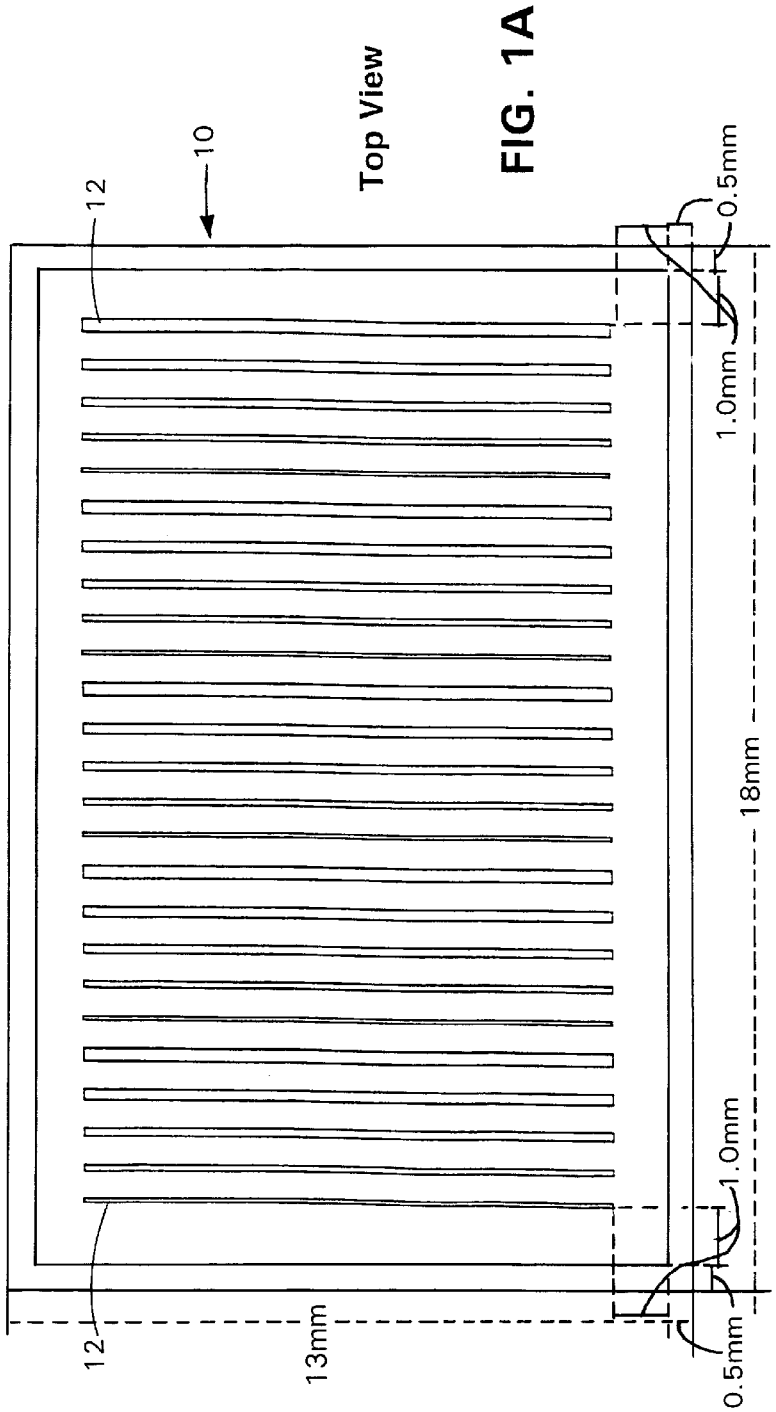
FIG. 1A
FIG. 1B

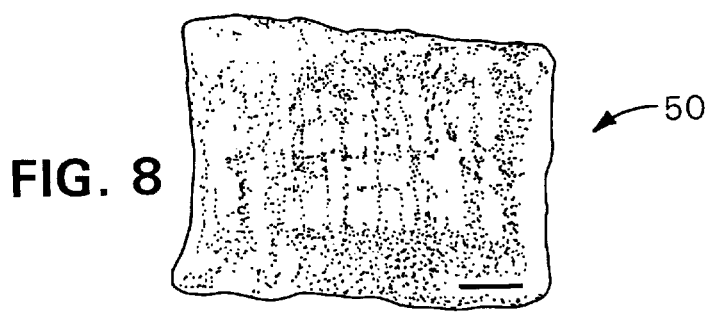
FIG. 8
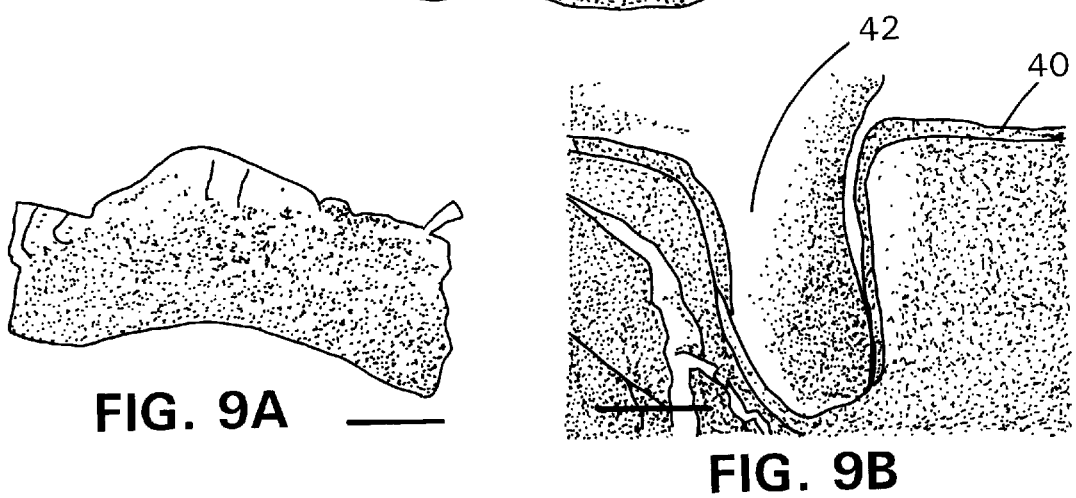
FIG. 9A
FIG. 9B
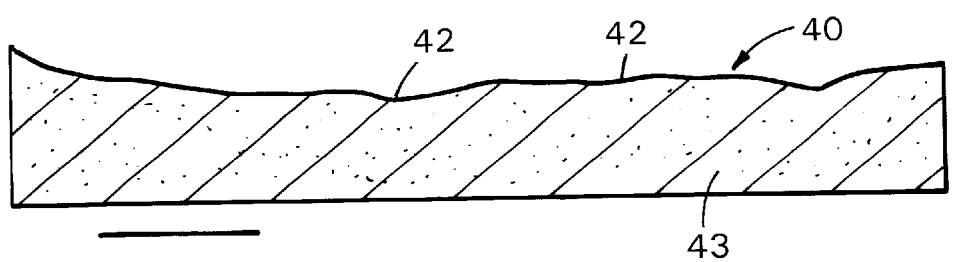
FIG. 10A
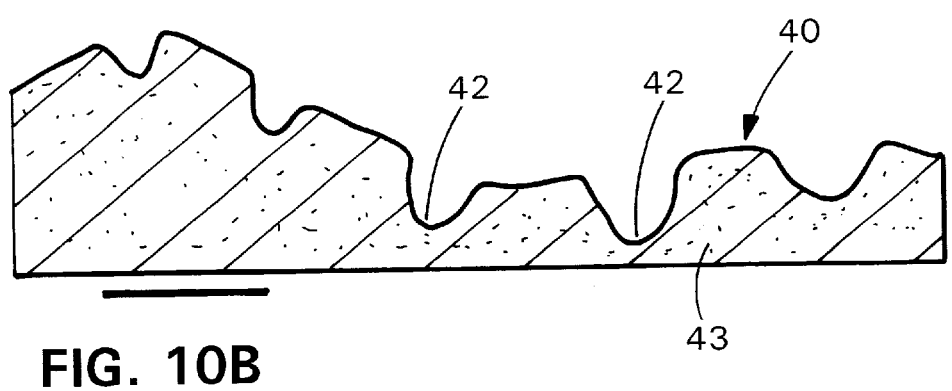
FIG. 10B

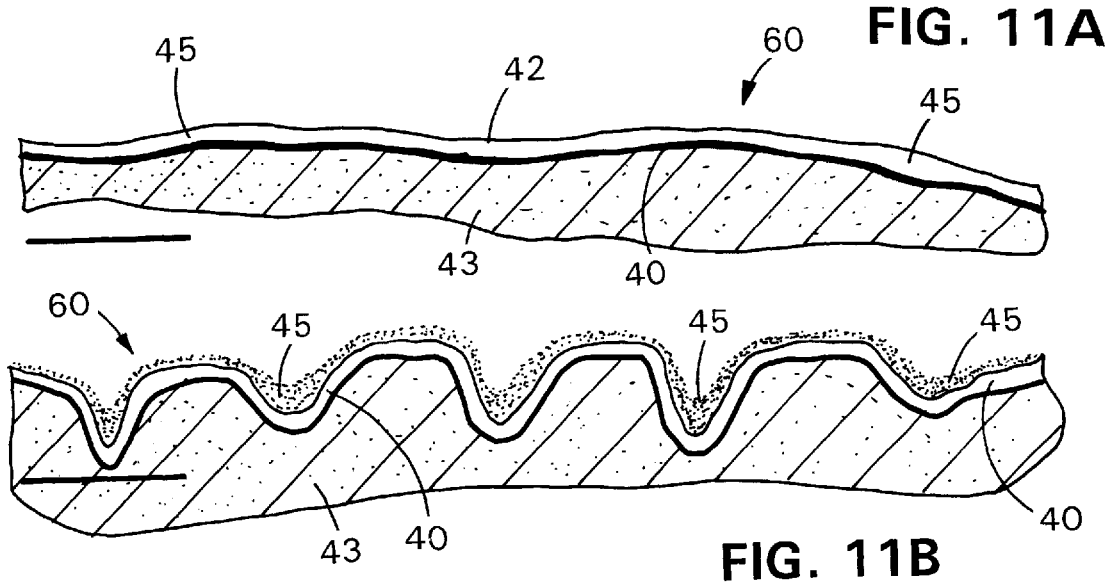
FIG. 11A
FIG. 11B
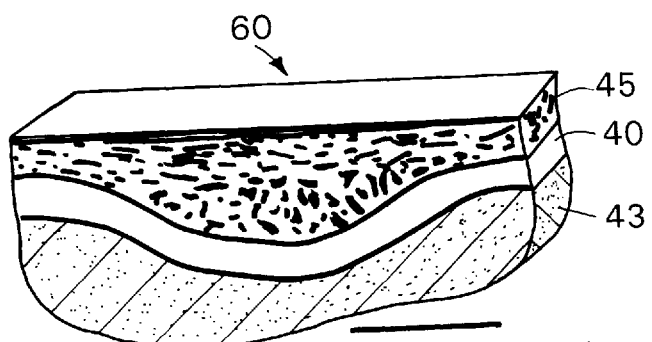
FIG. 11C
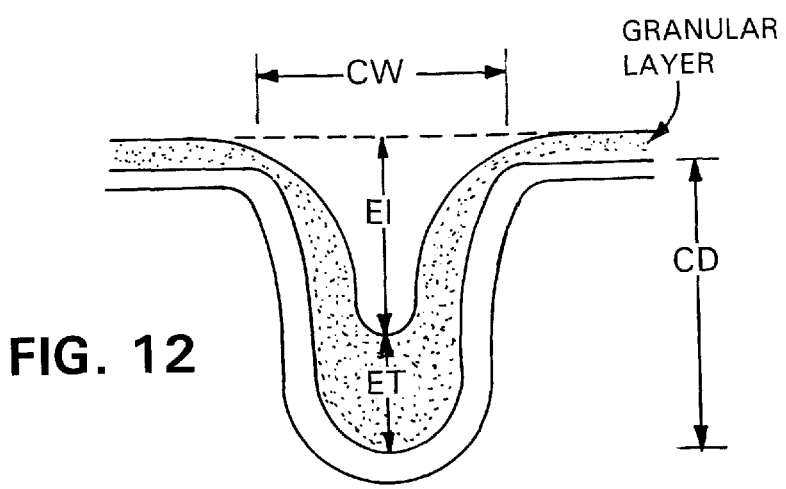
FIG. 12

MICROFABRICATED MEMBRANES AND MATRICES

CROSS-REFERENCE TO RELATED APPLICATION

This application claims benefit of priority from U.S. Provisional Patent Application No. 60/119,761, filed on Feb. 11, 1999, which is incorporated herein by reference in its entirety.

STATEMENT AS TO FEDERALLY SPONSORED RESEARCH

This invention was made, in part, with Government support under grant number R29 AR42012-01A1 awarded by the National Institutes of Health. The Government has certain rights in the invention.

FIELD OF THE INVENTION

The invention relates to the preparation of synthetic membranes, such as biocompatible membranes, and matrices.

BACKGROUND

Synthetic membranes have many uses, such as in the emerging field of tissue engineering. In general, engineered tissue analogs, often composed of cultured cells, biomaterials, or composites combining cells and biomaterials, have achieved some clinical success, for example, as substitutes for skin and cartilage.

Significant effort has been devoted to producing biocompatible scaffolds with defined pore sizes that help ensure proper cell-cell contacts, cell-matrix interactions, and to preserve cellular function. For example, collagen sponges and foams, cylindrical poly(l-lactic acid) (PLA) devices, and polyglycolic acid (PGA) fibers processed into porous, non-woven mesh matrices, have been made to provide substitute skin, nerves, and cartilage. Although sponges, foams, and matrices are useful for the fabrication of relatively large, three-dimensional tissue analogs, their use is limited for the creation of thin membranes such as the basal lamina, a membranous layer of connective tissue found in many organs and tissues.

The basal lamina or basement membrane is a thin membranous layer of connective tissue that underlies all epithelial cell sheets and tubes. For example, a basal lamina separates the endothelial cell layer of blood vessels from the underlying tissue and a basal lamina separates the epidermis from the underlying dermal tissue. A basal lamina also surrounds individual muscle cells, fat cells, and Schwann cells of nerve fibers. The basal lamina separates these cells and cell sheets from the underlying or surrounding connective tissue. In other locations, such as in the kidney glomerulus and lung alveolus, a basal lamina lies between two cell sheets and functions as a highly selective filter. Basal laminae serve more than structural and filtering roles. They are also able to determine cell polarity, influence cell metabolism, organize the proteins in adjacent plasma membranes, induce cell differentiation and serve as specific highways for cell migration. The basal lamina can also serve as a selective barrier to the movement of cells. The lamina beneath an epithelium, for example, usually prevents fibroblasts in the underlying connective tissue from contacting the epithelial cells, but does not prevent the movement of immune cells in and out of the epidermis, nor does it prevent the innervation of the epidermis. During wound healing as well as during normal development, the basal lamina acts as a guide and template that helps control cell migration and differentiation.

SUMMARY

The invention is based on the discovery that a membrane can be manufactured to have a highly controlled and complex three-dimensional topography by using microfabrication techniques. Similarly, a matrix can be manufactured to have a highly controlled and complex three-dimensional surface topography. The new microfabricated membranes and matrices can be prepared of man-made as well as natural materials, such as materials found in naturally occurring membranes, and thus can be made in the form of tissue substitutes or analogs, such as basal lamina analogs.

Given the important role of the basal lamina membrane in many different tissues and organs, the ability to produce basal lamina analogs with a controlled and complex three-dimensional topography has numerous applications in tissue engineering and the manufacture of artificial organs. Because of their carefully controlled and defined topographies and high surface areas, synthetic, microfabricated membranes can be used, for example, in air and water filters, cell culturing devices, and blood dialysis devices.

In general, the invention features microfabricated membranes including a sheet of conforming material that comprises a defined, three-dimensional topography, e.g., invaginations and/or projections. The membranes can be made of conforming materials such as gelatins, collagens, polyurethanes, polylactic acids, TEFLON®, polystyrenes, epoxy resins, methacrylates, polycarbonates, silicones, non-collagenous proteins, or polysaccharides. The membranes can also be made of copolymers, such as blends of polylactic acid and polyglycolic acid, or natural materials such as proteoglycans and glycosaminoglycans, as well as blends of natural and synthetic materials. The membranes can be, e.g., from 1 to 500, or 1 to 5, 10, 15, 20, 35, or 50 microns thick. The topographic features can have a height or depth of, e.g., 1.0 to 1000 microns, or 10 or 20 to 100 or 200 microns. The topographic features can have a width of, e.g., 1.0 to 500 microns, or 5, 10, or 20 to 100, 200, or 300 microns. The membranes can have a controlled porosity or permeability.

The invention also features new basal lamina analogs that include a microfabricated membrane, wherein the membrane is 1 to 50 microns thick, and the three-dimensional topography is defined to mimic the three-dimensional topography of a natural basal lamina.

In another aspect, the invention also features dermal or tissue analogs that include a polymeric matrix and a basal lamina analog fixed, e.g., laminated, to a surface of the polymeric, e.g., protein such as collagen, matrix. The polymeric matrix can include type I or type IV collagen and a glycosaminoglycan (GAG). The polymeric matrix can also be non-proteinaceous, and include, e.g., hyaluronic acid. The polymeric matrix can include any of the conforming materials mentioned herein that can be used to form the membranes.

The invention also features tissue substitutes including a dermal or tissue analog, and mammalian, e.g., human, canine, feline, bovine, equine, porcine, or ovine cells, e.g., epithelial cells, grown on and/or in the dermal analog. When the epithelial cells are keratinocytes, the tissue substitute is a skin substitute. In some embodiments, the mammalian cells are engineered to include a nucleic acid construct that encodes a heterologous polypeptide, or a therapeutic protein, a growth factor, a wound healing factor, or a hormone.

The invention also features a method of preparing a microfabricated membrane comprising a defined, three-dimensional topography, by preparing a master plate comprising a defined, three-dimensional pattern; transferring the pattern or a negative of the pattern to a membrane material; and allowing the membrane material to solidify, e.g., polymerize, harden, or gel, to form the microfabricated membrane, wherein the membrane has a defined, three-dimensional topography that is substantially the same as the three-dimensional pattern of the master plate or a negative of the master plate pattern.

The pattern can be transferred from the master plate to the membrane material by applying the material directly to the master plate, to produce a microfabricated membrane that has a defined, three-dimensional topography that is substantially the same as a negative of the three-dimensional pattern of the master plate. Alternatively, the pattern can be transferred from the master plate to the membrane material by coating the master plate with a liquid or semi-solid conforming material, e.g., polydimethyl-siloxane silicone elastomer (PDMS); allowing the conforming material to solidify, and removing the conforming material from the master plate to form a negative replicate that comprises a negative of the master plate pattern; applying a membrane material to the negative replicate; and allowing the membrane material to solidify to form the microfabricated membrane and removing the membrane from the negative replicate, wherein the membrane has a defined, three-dimensional topography that is substantially the same as the three-dimensional pattern of the master plate. The invention also includes microfabricated membranes prepared by the new methods.

In yet another embodiment, the invention covers a method of preparing a microfabricated tissue analog comprising a defined, three-dimensional surface topography, by preparing a master plate comprising a defined, three-dimensional pattern; transferring the pattern or a negative of the pattern to a matrix material; and allowing the matrix material to solidify to form the microfabricated tissue analog, wherein the analog has a defined, three-dimensional surface topography that is substantially the same as the three-dimensional pattern of the master plate or a negative of the master plate pattern. The invention also includes tissue analogs made by this method.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention provides several advantages. For example, the invention provides virtually unlimited design possibilities for the precise control of the three-dimensional topography of thin, synthetic membranes, such as biologically active membranes. Moreover, the new microfabricated, synthetic membranes can be prepared in the form of novel skin substitutes, which have applications in the treatment of burns, plastic surgery, ulcers, and gene therapy.

Other features and advantages of the invention will be apparent from the following detailed description, and from the claims.

BRIEF DESCRIPTION OF DRAWINGS

FIGS. 1a and 1b are schematic diagrams (top and side view, respectively) of a master pattern consisting of a series of parallel channels with varied widths and depths.

FIG. 8 is a top view of a rehydrated dermal analog produced by laminating a microfabricated membrane to the surface of a collagen-GAG sponge. The scale bar in the lower right corner represents 5.0 mm.

FIGS. 9a and 9b are schematics of scanning electron micrographs of a dermal analog at two different magnifications (19× and 490×, respectively). The scale bar represents 1.0 mm in FIG. 9a, and 50 microns in FIG. 9b.

FIGS. 10a and 10b are schematics of the cross-section of a dermal analog including a microfabricated membrane (having sets of channels designed to range from 40–200 microns in width and 40 microns in depth (FIG. 10a) and 200 microns (FIG. 10b) in depth) and a porous collagen-GAG sponge. The scale bar represents 500 microns in FIGS. 10a and 10b.

FIGS. 11a to 11c are a series of schematics of micrographs of a skin substitute including a layer of keratinocytes, a microfabricated membrane, and a porous collagen-GAG sponge. FIGS. 11a and 11b show a skin substitute with sets of channels designed to be 40 microns or 200 microns in depth, respectively. FIG. 11c shows differentiated and stratified keratinocytes in individual channels of a microfabricated membrane. Scale bars represent 500 microns in FIGS. 11a and 11b and 100 microns in FIG. 11c.

FIG. 12 is a schematic diagram showing the parameters used measure invaginations in epithelial layers formed on microfabricated membranes.

DETAILED DESCRIPTION

Figure 4:
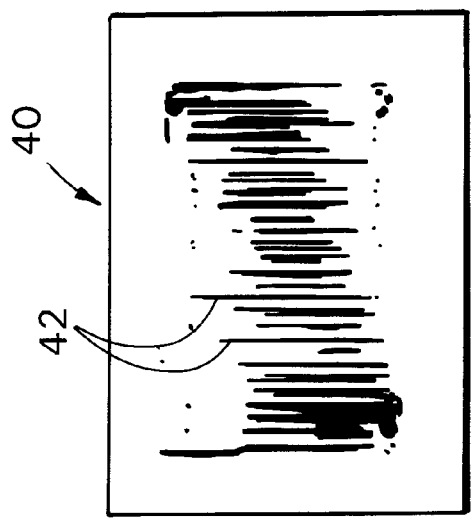
FIG. 4 is a diagram of a microfabricated membrane produced by air-drying a small volume of gelatin or collagen-GAG coprecipitated on the surface of the negative replicate.

The invention includes methods to produce microfabricated, synthetic membranes and matrices with controlled and complex three-dimensional topographies at the micron scale with sub-micron resolution; the microfabricated membranes, such as basal lamina analogs, and matrices produced by the new methods; and improved compositions, such as tissue analogs (e.g., dermal analogs and skin substitutes), that are made with the microfabricated membranes, e.g., basal lamina analogs, and matrices.

General Methodology

The new methods include three basic steps: (1) creating a master pattern, e.g., a three-dimensional pattern, (2) microfabricating a master plate or chip that corresponds to the master pattern (either as a duplicate or a negative of the master pattern), and (3) transferring the three-dimensional pattern of the master plate to a membrane, dense gel, or other matrix or substrate. The goal is to create a microfabricated membrane or matrix that has the same, or essentially the same, three-dimensional pattern as the master pattern. Thus, the third step can be performed by making the master plate a duplicate of the master pattern, then preparing a negative replicate from the master plate, and using the negative replicate to create the membrane. Alternatively, the master plate can be made as a negative of the master pattern, and used directly to cast the membrane.

The master plate or the negative replicate can also be used to imprint a defined, three-dimensional topography into a polymeric matrix, used as a dermal analog, for example, without a separate membrane. In this embodiment, a polymeric matrix is applied to the master plate or negative replicate in a liquid or semi-solid state, and conforms to the pattern. It is solidified and then removed to provide the patterned matrix.

Microfabricating the Master Plate

The production of a microfabricated membrane begins with the design of a master pattern that includes the desired three-dimensional surface topography for the membrane. The master pattern can be drawn out, e.g., by hand or using a CAD-CAM device, or programmed into a computer, or both. The range of sizes of surface features over which the methods can be used to control the topography of the new membranes ranges from the submicron scale to microns, or tens or hundreds of microns (and even millimeters). The range was tested by use of a test pattern.

FIGS. 1a and 1b show a master pattern 10 having channels 12 of different depths and widths. The test pattern was prepared to have a series of 25 parallel channels 12 (10 mm long) in groups of five with each channel in a group having the same depth, and each group having a different depth ranging from 40 microns to 200 microns. Within each group, the five channels had widths ranging from 40 microns to 200 microns.

The master pattern is then used to generate a master plate or chip, by programming a microfabrication device to create the features of the master pattern (or a negative of the master pattern) in a three-dimensional, solid material. The master plate can be machined from various metals and metal oxides such as alumina, ceramics, diamond, polymers like polyimide, quartz, glass, and silicon.

Figure 2:
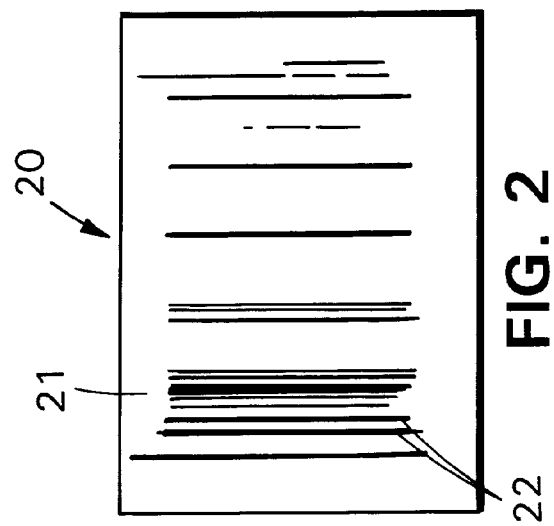
FIG. 2 is a diagram of a master chip or plate made by laser machining the channels specified in the master pattern in FIGS. 1a and 1b into the surface of a polyimide chip. The scale bar represents 5 mm.

For example, as shown in FIG. 2, a master plate 20 was produced by laser machining the specified channels 12 of the master pattern 10 into a polyimide chip 21 (1.0 mm thick, Goodfellow Corp., Berwyn, Pa.) using an excimer laser (Potomac Photonics, Inc., Lanham, Md.). Briefly, rectangular images of an excimer laser beam were line focused (10 mm×40 $\mu$m) onto the surface of a polyimide chip 21, and then the laser energy was pulsed at 10 mJ, at an energy of 2 to 3 J/cm$^2$, and at a pulse rate of 100 Hz to ablate its surface. The image of the laser beam was repositioned and the process was repeated until all channels 22 with the specified geometries were machined.

Numerous other microfabrication technologies and materials can be used to produce a master pattern with micron size and smaller dimensions. Examples include microetching and micromachining of metallic, metal oxide (e.g., alumina), ceramic, glass, or polymeric surfaces (e.g., polyimide), as well as the widely used photo-, x-ray- or UV-lithography methods used to make micropatterns on the surface of silicon, or other semiconductors used in the manufacture of computer chips. For a review of various microfabrication techniques including photolithography, oxidation, layer deposition, and etching, see Chapter One of Maly, "Atlas of IC Technologies: An Introduction to VLSI Processes," The Benjamin/Cummings Publishing Company, Inc., Menlo Park, Calif., 1987.

Microstructures can also be fabricated using photosensitive polyimide electroplating molds. For example, see, Frazier et al., J. Microelectromechanical Systems, 2:87–94 (I.E.E.E., 1993). Standard reactive ion etching and the black silicon method can also be used to fabricate microstructures in silicon having high aspect ratios and smooth surface textures. See, e.g., Jansen et al., "The Black Silicon Method IV," J. Microelectromechanical Systems, 88–93 (I.E.E.E., 1995).

In addition to channels, other types of structures, patterns, and biological designs can be machined into the master plate.

For example, to create a synthetic membrane to serve as a basal lamina analog, the peaks and valleys of the three-dimensional surface topography of the membrane should mimic the three-dimensional surface of a naturally occurring basal lamina, e.g., the lines of the hands or fingerprints for basal lamina that are used to prepare skin substitutes for the hand or fingers. For use in water filtration devices, the synthetic membranes can have a straight channel design such as the test pattern described above (but with all channels being of equal depth and width), or can have spiral or serpentine channels to provide a significantly long path length relative to the total area of the membrane through which the water can flow.

For size exclusion filtration, the microfabricated membranes can be made with pores with highly accurately size control. To make such membranes, the master plate is prepared with numerous circular plateaus or spikes, e.g., that remain when the remainder of the plate surface is etched away. See, e.g., Henry et al., J. Pharmaceutical Sciences, 87:922–925 (1998), and Jansen et al., "The Black Silicon Method IV," J. Microelectromechanical Systems, 88–93 (I.E.E.E., 1995). The plateaus or spikes are designed to have a height greater than the desired thickness of the membrane. The membrane is cast directly from the master plate, and the conforming material used to prepare the membrane is applied to the master plate so that the tops of the plateaus remain exposed. When the membrane material solidifies, the membrane will have pores with precisely controlled pore sizes and locations. Alternatively, the master plate can have precise circular wells or cones cut into its surface, a negative replicate is created that has round plateaus or spikes, and the microfabricated membrane is cast form the negative replicate.

Figure 5:
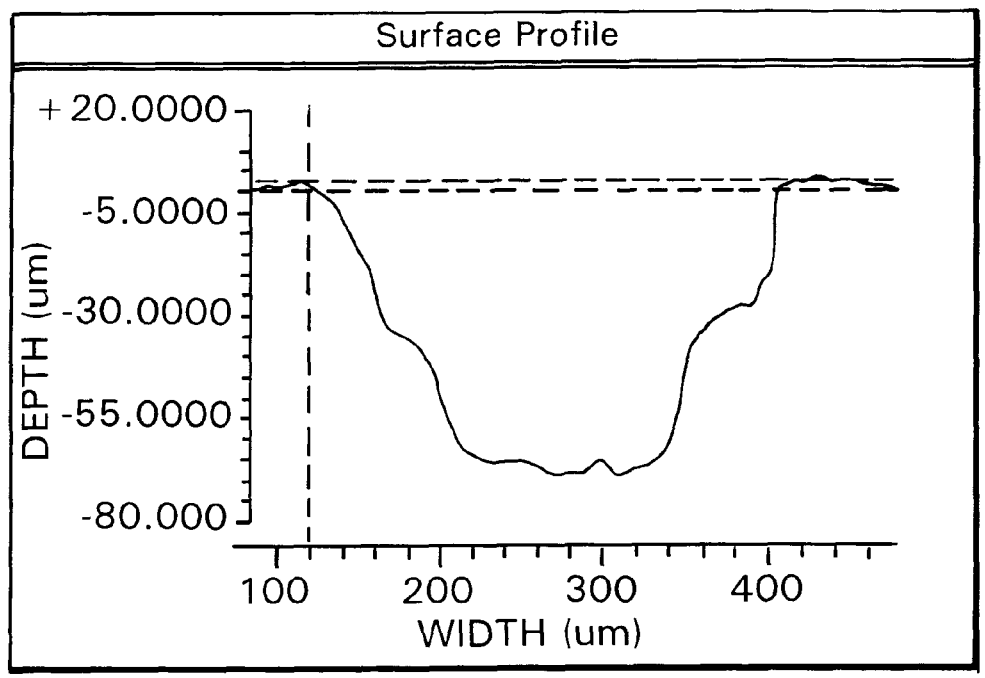
FIG. 5 is a computer-generated, two-dimensional surface profile of a channel in the master plate, which can be used to measure the width and depth of each channel.
Figure 6:
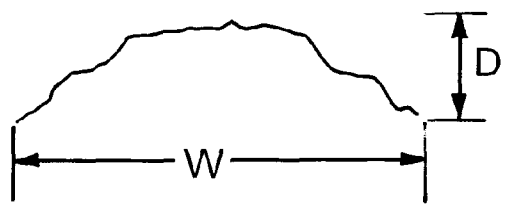
FIG. 6 is a schematic representation of a section cut perpendicular to the surface of a negative replicate, which shows the width (W) and depth (D) of the protruding ridges that match the channels cut into the master plate. The scale bar represents 250 microns.
Figure 7A:
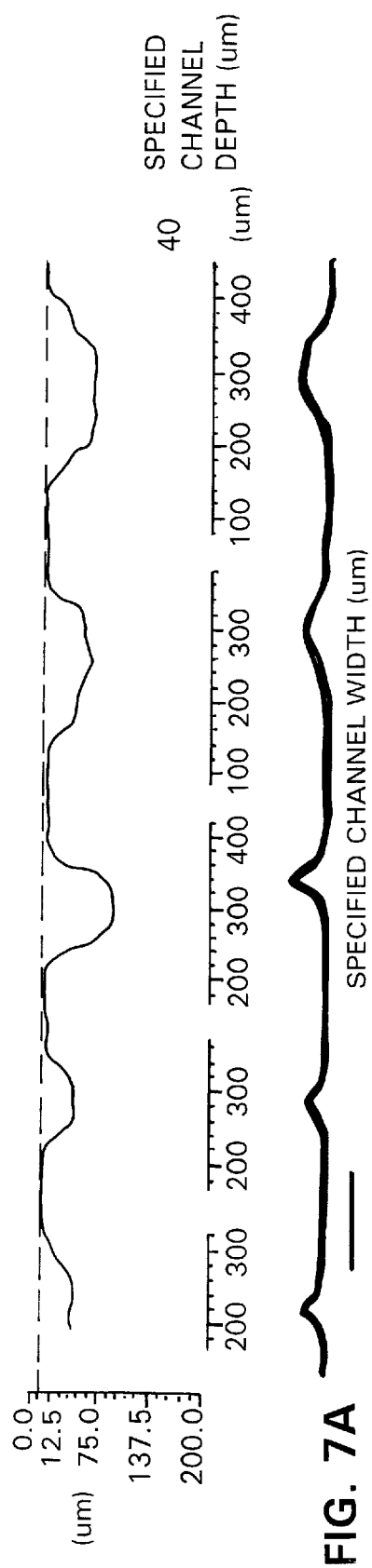
FIGS. 7a to 7e are a composite series of surface plots of the master plate and photographs of the negative replicates comparing the dimensions of each protruding ridge of the negative replicate with the surface profile of the corresponding channel in the master chip. The scale bars represent 250 microns.
Figure 7B:
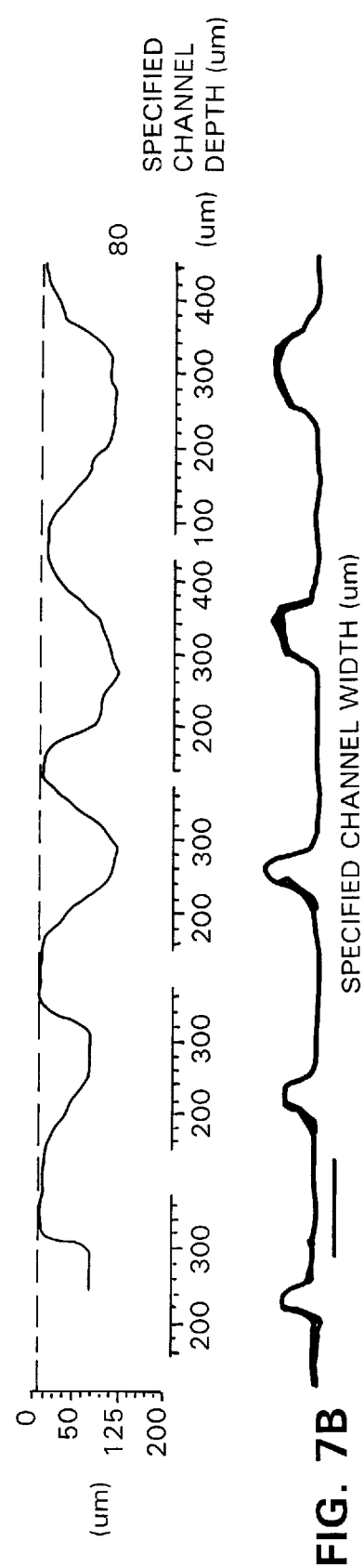
Figure 7C:
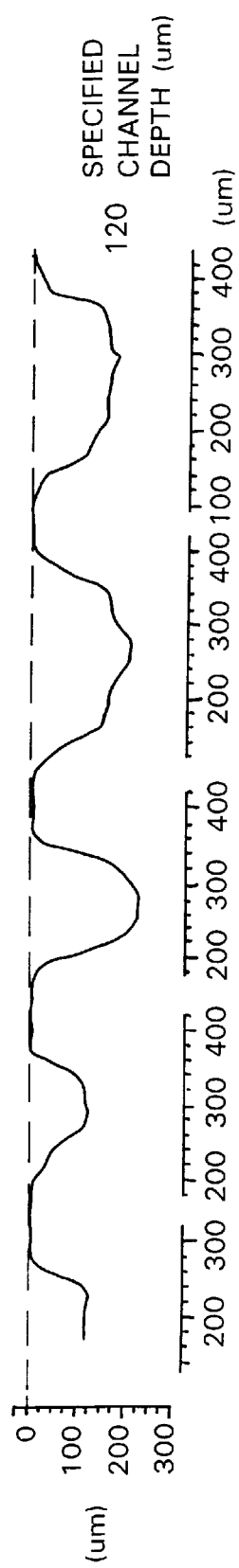
Figure 7D:
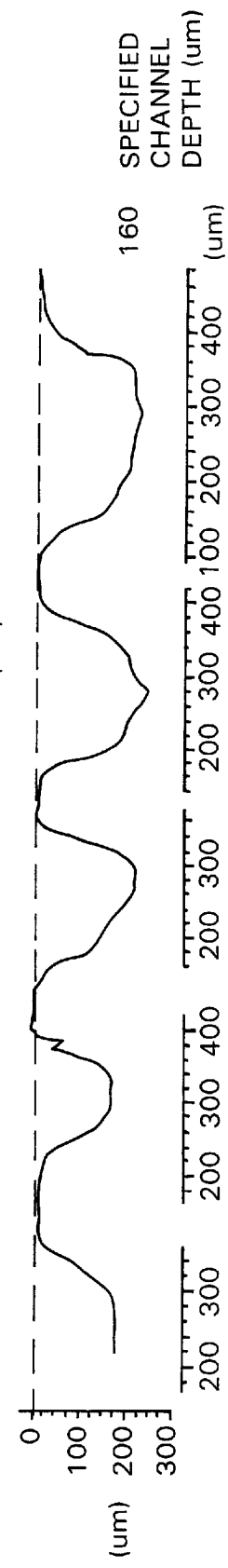
Figure 7E:
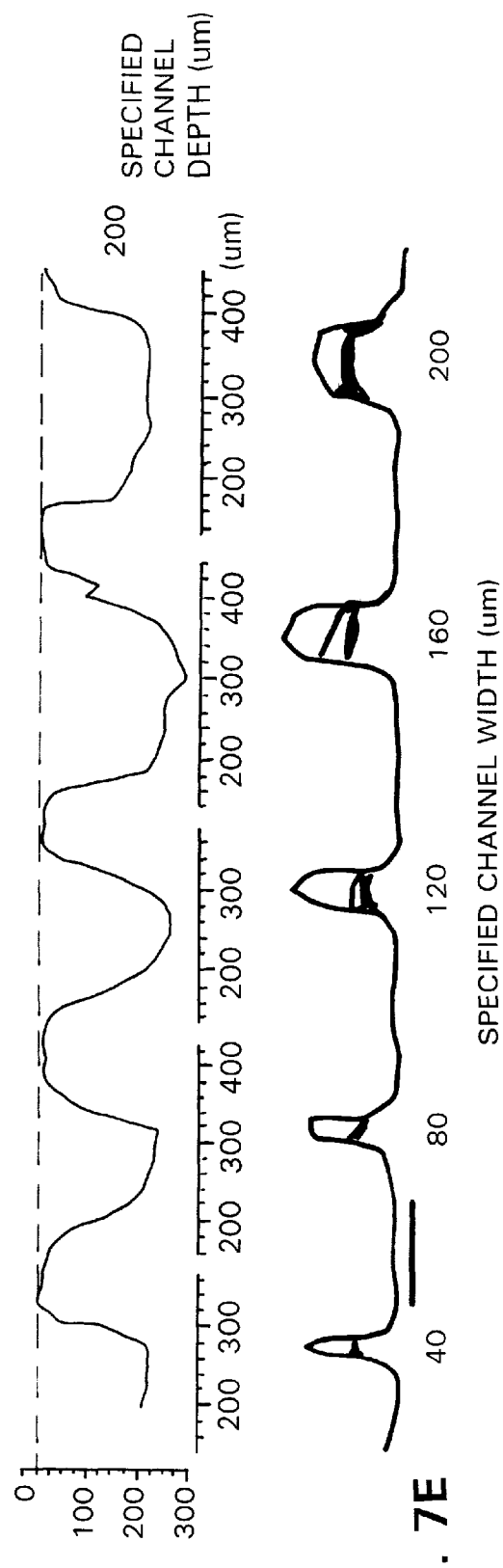

To test the fidelity with which laser machining had reproduced the specifications of the master pattern, the dimensions of the channels in the master plate (chip) were analyzed with a Zygo New View 200 Scanning White Light Interference (SWLI) Microscope (Zygo Corp., Middlefield, Conn.) fitted with a 20× Mirau objective lens. The microscope produced three-dimensional images of each channel and two-dimensional surface profiles in planes perpendicular to the surface of the master chip. The shoulder-to-shoulder widths and maximum depths of each channel were measured with the caliper tools in the microscope software. FIG. 5 is a computer-generated plot of the surface profile of a channel in the master plate.

Analyses of this data indicated that the shoulder-to-shoulder widths of the channels in the master chip ranged from 114–310 microns, deviating from the 40–200 microns channel widths specified in the master pattern. Nevertheless, the varied channel widths in the master plate were useful to carry out further tests, and the deviation merely indicated that the laser etching had not be performed with a high degree of accuracy.

The maximum depths of the channels also deviated from the original master pattern. The depths of the narrowest channels deviated from the specified 40 or 80 microns by less than 14%, but the depths of the wider channels deviated from the specified 120, 160, or 200 microns by 28 to 133%. The three-dimensional images obtained by SWLI microscopy also showed that, unlike the flat bottoms of our original design, the bottom surfaces of the wider channels (specified 120, 160 or 200 microns) tapered to points or had serrated and irregular surfaces. In addition, the widest channels (specified 200 microns) had notched shoulders in the side walls. In spite of these irregularities, these master plates were useful to prepare negative replicates. In fact, the irregularities were replicated in the final microfabricated membranes, providing evidence that even details at the micron and submicron level can be recreated using the new methods of preparing membranes.

Laser etching can provide higher degrees of accuracy, and other microfabrication techniques discussed herein can also be used to provide a greater degree of accuracy.

The degree of accuracy can be varied according to the manufacturing technique and cost, and according to the intended use of the microfabricated membranes made with the master plate. For example, if a membrane is to be used in certain tissue substitutes, for example, the master pattern should be recreated with a high degree of accuracy, e.g., 90 percent or higher. For use in water filtration or other mechanical devices, the degree of accuracy may be lower, e.g., 75, 80, or 85 percent.

Preparing Negative Replicates

In the next step, which is optional, a negative replicate is made using the master plate. To make a negative replicate, a solution of liquid or semi-solid plastic or resin is applied to the master plate and allowed to solidify. The solid plastic is then removed to form the negative replicate, which has a negative imprint of the master pattern as machined into the master plate. Many materials can be used to prepare the negative replicate. The main features of these materials are that they can conform to the master plate, i.e., fill the three-dimensional topography, and that they can thereafter solidify in some way. The materials must also be separable from the master plate after they have solidified. This can be achieved by judicious selection of the materials used for the plate and the negative replicate, and can be assisted by the use of release agents sprayed onto the plate.

Various materials can be used as the conforming material, many of which are polymeric. Polyurethanes, polylactic acids, TEFLON®, polystyrenes, epoxy resins, methacrylates (e.g., polymethylmethacrylates), polycarbonates, silicones, collagens, gelatins, glycosaminoglycans, proteoglycans, and polysaccharides are all useful examples. Other materials are known, such as copolymers, e.g., of polylactic acid and polyglycolic acid, or blends of natural and synthetic materials, and can be used.

The negative replicates can be solidified using various techniques, and depends on the specific conforming material used. For example, the conforming material can be solidified by heating or cooling, by changing the ambient pressure, by UV or other curing, by activation of a catalyst, e.g., by heat or light, or by cross-linking, e.g., with formaldehyde, glutaraldehyde, UV, or carbodiimide. Other techniques are known to those of skill in this field.

Figure 3:
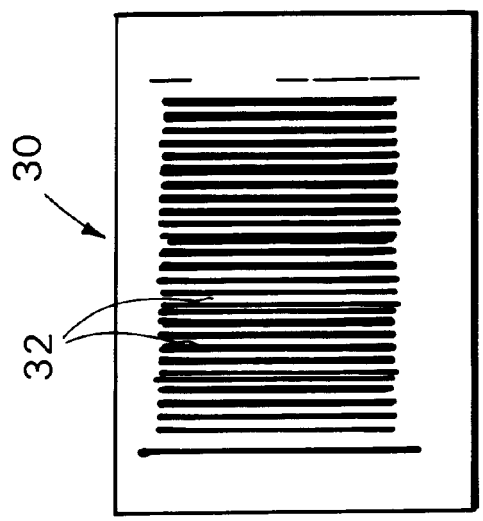
FIG. 3 is a diagram of a negative replicate formed by curing polydimethylsiloxane (PDMS) on the surface of the master chip. The scale bar represents 5 mm.

A negative replicate was made by pouring a polydimethylsiloxane silicone elastomer (PDMS, Sylgard 184, Dow Corning Corp., Midland, Mich.) over the master plate and polymerizing the elastomer by incubating at 65° C. for 2 hours. The PDMS overlay, which conformed to the fine three-dimensional features (e.g., channels) of the master plate, was carefully separated from the chip. As shown in FIG. 3, the resulting negative replicate 30 had surfaces of protruding ridges 32 that were an exact negative replicate of the channels 22 cut into the surface of the master plate 20 (FIG. 2).

To determine whether the PDMS faithfully reproduced the channels in the master chip, the dimensions of the protruding ridges on the surface of a negative replicate were analyzed with a Nikon Diaphot 300 microscope coupled with MetaMorph Imaging Software (West Chester, Pa.). Sections of a negative replicate were collected by cutting samples in a plane perpendicular to the microfabricated surface with a razor blade. Sections were placed on glass slides, viewed with a low power objective lens and digitally imaged with the microscope software. Shoulder-to-shoulder widths and maximum depths of each channel were measured with the tools provided in the software package.

The results are shown in FIGS. 6 and 7a to 7e. The shoulder-to-shoulder widths and the maximum heights of the protruding ridges replicated the channels in the master chip with an accuracy greater than 91% (analyses not shown).

Using the new methods it is possible to produce many negative replicates of a single master pattern, for example, to prevent the master plate from being worn out too rapidly if used to cast membranes directly without a negative replicate.

Preparing Microfabricated Membranes and Matrices

In the final step, the synthetic membrane is created by applying a conforming material in a liquid or semi-solid state to the negative replicate (or directly to the master plate if no negative replicate is used), and then allowing the material to solidify to its final consistency. The conforming materials used to prepare the microfabricated membranes can be selected from the same set of conforming materials used to make the negative replicates, but will generally be applied thinly to provide a thin membrane (e.g., 5, 10, 15, 20 microns thick, or more in certain embodiments) rather than applied more thickly to provide a more solid structure for the negative replicate. The conditions used to solidify the conforming membrane materials depend on the material used, and are the same as the conditions described herein for preparing the negative replicate. In one manufacturing run, the negative replicate and the membrane can be made of the same or different materials.

Once solidified, the synthetic, microfabricated membrane can be removed from the negative replicate. Some membranes are rigid, while others can be flexible or rubbery in consistency, depending on their intended utility. In all cases, the synthetic membranes have a three-dimensional surface topography that is substantially a negative of the surface topography of the negative replicate, and thus a topography that is substantially identical to the topography of the master plate, and to the master pattern. The degree of similarity or identity between the membrane and the master plate can vary, and can be more or less critical depending on the use of the membrane. In some uses, for example, filtration, the precise topography, e.g., of pores in the membrane, can be critical, and thus the membrane should have a very high degree of similarity to the master plate, and ideally to the master pattern, e.g., 95 percent or higher. In other uses, the degree of similarity is not as important, e.g., for certain basal lamina analogs (as describe herein), where the precise configuration is not as important as the overall three-dimensional nature of the topography.

Basal Lamina Analogs

As with most tissues, the basal lamina in the skin is not a simple flat plane of connective tissue, rather it conforms to a series of ridges and invaginations known as rete ridges and papillary projections. The depth and patterns of these ridges and invaginations of epidermis and dermis make important contributions to the function of the skin. For example, rete ridges are deep and numerous in the palms of the hands and soles of the feet and serve to significantly increase the surface area of contact between the epidermis/dermis, thus providing strong resistance to the shear forces experienced by the hands and the feet. The pattern of ridges and projections between the epidermis/dermis are also a significant part of the underlying features that contribute to the gross outward appearance of skin in the form of fine lines, small pores, and natural wrinkles. In addition, the adnexal structures of skin (hair and sweat glands) are deep invaginations of the epidermis into the dermis and a basal lamina conforms to these structures as well.

In addition to effects on the biomechanical properties of the skin, the pattern and depths of these ridges are thought to have a role in the proliferation and differentiation of epidermal keratinocytes. The fabrication of a basal lamina analog with controlled dimensions would help elucidate the influence of topography on cell function and has applications in tissue engineering of skin substitutes as well as other basal lamina containing tissues.

To form microfabricated basal lamina analogs, two types of materials were used with the negative replicates: gelatin or a white coprecipitate containing type I collagen (5 mg/ml) and glycosaminoglycan (GAG, 0.18 mg/ml). A 1% (w/v) gelatin solution was prepared by stirring 1.0 g of gelatin (Sigma Chemical, St. Louis, Mo.) into 100 ml of a 0.05 M acetic acid solution that was warmed to 65° C. until the gelatin was completely dissolved. The coprecipitate was prepared according to published protocols (Chamberlain, L. J. and Yannas, I.V. (1998) Preparation of collagen-GAG copolymers for tissue regeneration. In Tissue Engineering Methods and Protocols (Morgan, J. R. and Yarmush, M. L., eds) pp. 3–17, Humana Press, Totowa, N.J.). Briefly, 3.6 g of lyophilized bovine collagen (Medicol F, Integra Medicus, West Chester, Pa.) were dispersed in 600 ml of a 0.05 M acetic acid solution by blending at 20,000 rpm for 90 minutes at 4° C. in a refrigerated homogenizer. The coprecipitate was formed by adding 120 ml of a 0.11% w/v solution of shark cartilage chondroitin 6-sulfate (Sigma Chemical) to the blending collagen dispersion, and then blending the collagen-GAG copolymer for an additional 90 minutes. The collagen-GAG dispersion was degassed under vacuum to remove trapped air, and then stored at 4° C.

To create membranes, a small volume of either gelatin or collagen-GAG dispersion (220–330 ml/cm$^2$) was poured onto the PDMS negative replicate where it conformed to the surface. The dispersion was air dried at room temperature in a laminar flow hood and the resulting dried collagen membrane was gently peeled from the negative replicate. Finally, dried membranes were covalently crosslinked by thermal dehydration at 105° C. in a vacuum of 100 mTorr for 24 hours.

As can be seen in FIG. 4, the resulting basal lamina analog 40 contains a series of channels 42 substantially identical to the channels 12 in the master pattern 10 and the master plate 20.

Many materials other than collagen type I and GAGs can also be used to make basal lamina analogs. Examples include naturally occurring substances such as gelatin and purified basement proteins (laminin, collagen type IV, heparin sulfate proteoglycan, entactin, fibronectin, and nidogen) as well as biocompatible synthetic materials such as polylactic acid or copolymers of polylactic acid and polyglycolic acid, as well as blends of natural and synthetic materials. See, e.g., Boyce, U.S. Pat. No. 5,273,900 (column 7), which describes the use of bovine collagen and mucopolysaccharides such as GAGs like chondroitin-6-sulfate. See, also, Kleinman et al., U.S. Pat. No. 4,829,000.

In addition, negative replicates can be used to produce topographic patterns on microfabricated membranes made of other conforming materials that do not require a drying step. One useful example is gelled collagen.

Dermal and Other Tissue Analogs

Dermal or other tissue analogs can be prepared by combining a microfabricated basal lamina analog with an analog of tissue normally underlying the natural basal lamina. The basal lamina analog is attached to the surface, e.g., laminated as described in Boyce, U.S. Pat. No. 5,273,900 (columns 7–9), of the tissue analog to provide a composite synthetic tissue.

Composite dermal analogs were prepared by laminating a microfabricated basal lamina analog to the surface of a collagen sponge. The collagen sponge was produced by methods similar to those previously described by Yannas et al., "Design of an Artificial Skin, II. Control of Chemical Composition," *J. Biomed. Mater. Res.*, 14:107–131 (1980), and Boyce et al., "Structure of a Collagen-GAG Dermal Skin Substitute Optimized for Cultured Human Epidermal Keratinocytes," *J. Biomed. Mater. Res.*, 22:939–957 (1988). See also, Boyce, U.S. Pat. No. 5,273,900 (column 7). Briefly, 10 ml of a collagen-GAG dispersion were poured into an aluminum pan with a surface area of 38.5 cm$^2$ (Fisher Scientific, Springfield, N.J.), and a microfabricated basal lamina analog was gently floated on the surface of the dispersion. The GAG was chondroitin-6-sulfate, but others can be used.

The dispersion was rapidly frozen at −80° C., placed on a shelf in a freeze dryer initially set at −45° C., then lyophilized overnight (Virtis Genesis, Virtis, Gardner, N.Y.) at a vacuum of 100 mTorr. After lyophilization, the composites were covalently crosslinked by thermal dehydration at 105° C. in a vacuum of 100 mTorr for 24 hours, rehydrated in a 0.05 M acetic acid solution for 24 hours, crosslinked in a 0.25% glutaraldehyde solution for 24 hours, and then washed exhaustively with sterilized water, phosphate buffered saline and keratinocyte seeding medium (described below).

A top view of the rehydrated dermal analog 50 is shown in FIG. 8. FIGS. 9a and 9b show schematics of electron microscope photos of cross sections of the dermal analog at different magnifications. FIG. 9a shows numerous channels 42 of varying depths, and FIG. 9b shows a cross-section of the basal lamina analog 40 (microfabricated membrane) and one channel 42. The scale bar represents 1.0 mm in FIG. 9a, and 50 microns in FIG. 9b.

To determine whether the microfabricated membranes 40 faithfully reproduced the surface of the negative replicates, the dimensions of the channels were measured. Dermal analogs were fixed, embedded in glycolmethacrylate and 5 microns sections were cut perpendicular to the surface and were stained with hematoxylin and eosin. Histological observations showed that the dermal analog was composed of a 25 microns thick microfabricated membrane, with 25 channels of various widths and depths, that was supported by a porous collagen-GAG sponge. The channels in the membrane exhibited progressive increases in width and depth that were consistent with the corresponding ridges in the negative replicate. FIG. 10a shows very shallow channels 42 at one end of the analog, while FIG. 10b shows more significant channels 42 at the other end. Collagen sponge material 43 is also shown. Many of the small irregular surface features that were present in the master chip, such as serrated bottom surfaces, were also replicated in the membranes.

Tissue analogs can also be prepared without a microfabricated membrane on their surface, but still having a controlled three-dimensional surface, by applying the analog matrix, e.g., collagen gel, directly to the master plate or negative replicate in the desired thickness. The matrix material is allowed to solidify, and the resulting analog is removed and maintains the three-dimensional pattern of the master plate or pattern. Such matrices can be made of dense gels, such as collagen gels or hydrogels. Polymeric 2-hydroxyethyl-methacrylate (pHEMA) can be used to prepare such matrices and membranes.

Skin and Other Tissue Substitutes

The final step to make a skin or other tissue substitute is to seed the surface and/or interior of a dermal or other tissue analog with cultured mammalian cells, e.g., human cells, such as epithelial cells, e.g., epidermal cells, keratinocytes, lung cells, blood vessel cells, kidney cells, dermal cells, or other cells such as fibroblasts, nerve cells, and hair follicle cells.

To prepare a man-made or synthetic human skin substitute, normal human keratinocytes derived from neonatal foreskins were cultured by the method of Rheinwald and Green, "Formation of a Keratinizing Epithelium in Culture by a Cloned Cell Line Derived from a Teratoma," *Cell*, 6:317–330 (1975). Keratinocytes were co-cultivated with 3T3-J2 mouse fibroblasts, which had been pretreated with 15 mg/ml mitomycin C (Boehringer Mannheim Co., Indianapolis, Ind.). Culture medium was changed every 3–4 days with a 3:1 mixture of Dulbecco's modified Eagle's medium (DMEM) (high glucose) (GIBCO-BRL, Gaithersburg, Md.) and Ham's F-12 medium (GIBCO-BRL) with 10% fetal bovine serum (FBS, JRH Bioscience, Lenexa, Kans.). Supplements such as adenine, hydrocortisone, cholera toxin, insulin, transferrin, triiodo-L-thyronine, and penicillin-streptomycin, were added as described in Medalie et al., *J. Invest. Dermatol.*, 107:121–127 (1996).

Cells were subcultured by first removing the feeder layer cells with a brief EDTA wash, 5 mM in phosphate-buffered saline (PBS), and then treating the keratinocytes with trypsin-EDTA.

Keratinocytes were seeded onto the dermal analogs using methods similar to those previously described (Medalie et al., *Transplantation*, 64:454–465, 1997) with media changes as described by Ponec et al., *J. Invest. Dermatol.*, 109:348–355 (1997). Dermal analogs were placed into 35-mm tissue culture dishes, microfabricated membrane side up, and cells in keratinocyte seeding medium (described below) were seeded onto the surface ($5 \times 10^5$ cells/cm$^2$). After approximately 2 hours, the cell-seeded dermal analogs were submerged in keratinocyte seeding medium for 24 hours. Keratinocyte seeding medium was a 3:1 mixture of Dulbecco's modified Eagle's medium (high glucose) (GIBCO-BRL) and Ham's F-12 medium (GIBCO-BRL) supplemented with 1% FBS (JRH Bioscience), 10-10 M cholera toxin (Vibrio Cholerae, Type Inaba 569 B; Calbiochem, La Jolla, Calif.), 0.2 mg/ml hydrocortisone (Calbiochem), 5 mg/ml insulin (Novo Nordisk, Princeton, N.J.), 50 mg/ml ascorbic acid (Sigma Chemical) and 100 IU/ml, and 100 mg/ml penicillin-streptomycin (Boehringer Mannheim Co.).

After 24 hours, the keratinocyte seeding medium was removed, and the skin equivalents were submerged for an additional 48 hours in a keratinocyte priming medium. Keratinocyte priming medium was composed of keratinocyte seeding medium supplemented with 24 mM bovine serum albumin (Sigma Chemical), 1.0 mM L-serine (Sigma Chemical), 10 mM L-carnitine (Sigma Chemical), and a cocktail of fatty acids including 25 mM oleic acid (Sigma Chemical), 15 mM linoleic acid (Sigma Chemical), 7 mM arachidonic acid (Sigma Chemical), and 25 mM palmitic acid (Sigma Chemical). See, Boyce and Williams, *J. Invest. Dermatol.*, 101:180–184 (1993).

After 48 hours in priming medium, skin equivalents were placed on stainless steel screens, raised to the air-liquid interface and cultured for 7 days with an air-liquid interface medium composed of serum-free keratinocyte priming medium supplemented with 1.0 ng/ml epidermal growth factor (Collaborative Biomedical Products, Bedford, Mass.).

Other materials can be used to make dermal analogs and basal lamina analogs can be used as part of the construction of tissues other than skin.

Histological and Quantitative Morphometric Analyses

For histological analysis, skin substitutes were fixed in a 3% glutaraldehyde/4% paraformaldehyde solution, dehydrated with increasing concentrations of ethanol, infiltrated first at −80° C. and then at 4° C. with glycolmethacrylate (JB-4, Polysciences, Inc., Warrington, Pa.), and finally embedded in glycolmethacrylate. Sections of skin equivalents, 5 mm thick, were collected by cutting samples in a plane perpendicular to the surface of the microfabricated membrane. Sections were mounted on glass slides with Tissue-Tack Adhesive (Polysciences, Inc.), stained with Gill's hematoxylin and ethanolic eosin solutions, and then viewed with a Nikon Eclipse 800 microscope.

For scanning electron microscopy, skin equivalents were fixed in a 3% glutaraldehyde/4% paraformaldehyde solution, post fixed with a 1% osmium tetroxide solution, en bloc stained with a 2% uranyl acetate solution, dehydrated with increasing concentrations of ethanol, then critical point dried with liquid carbon dioxide under pressure. Samples were sputter coated with a thin layer of gold-palladium and viewed with an Amray 1000 scanning electron microscope.

As shown in FIGS. 11a to 11c, histology showed that the surface of the skin substitutes 60 contained a series of ridges (channels) 42 of varying heights and widths and that these ridges as well as the spaces between the ridges were covered with one or more stratified epidermis layers 45. Depending on its depth as well as its width, each ridge had an epidermis with different numbers of stratified layers. Epidermal thickness of the flat inter-ridge areas was about 37 microns, and the thickness increased as the depth of each channel increased. Deeper ridges contained more cells and had more stratified layers than shallow ridges as well as the flat inter-ridge areas. In addition, the top surface of the cornified layers conformed to the channels as well as the inter-ridge pattern and created a macroscopic pattern. Infolds of the epidermis occurred when the depth of the channels were greater than about 25 microns, and these invaginations increased in size as channel depth increased. Thus, some of the channels of the master pattern were deep enough to create gross topological features obvious to the naked eye.

Specifically, low magnification micrographs show a skin substitute 60 with a basal lamina analog 40 having sets of channels 42 designed to be 40 microns (FIG. 11a) or 200 microns (FIG. 11b) in depth. Dermal analog 43 is located beneath the basal lamina analog, while keratinocytes form epidermal layers 45 above the basal lamina analog 40. High magnification micrographs show differentiated and stratified keratinocyte layer 45 in individual channels 42 of a microfabricated membrane 40 (FIG. 11c). Scale bars represent 500 microns in FIGS. 11a and 11b and 100 microns in FIG. 11c.

Figure 13A:
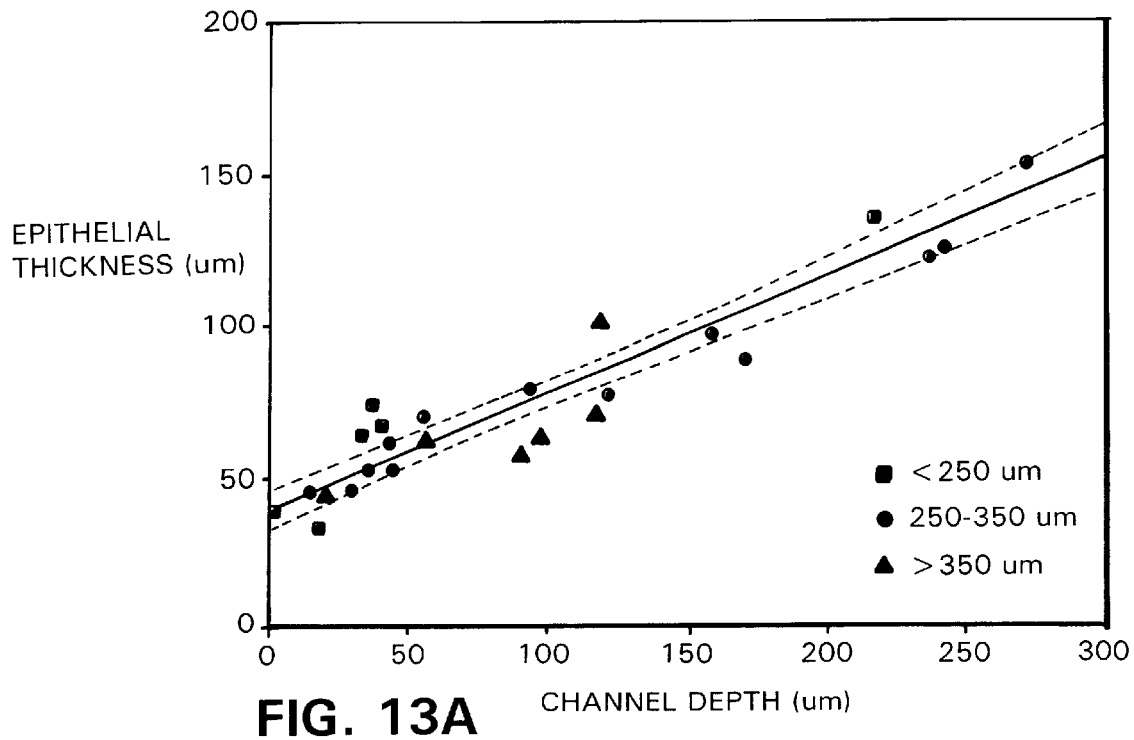
FIGS. 13a and 13b are two graphs showing epithelial thickness and epidermal invagination depth, respectively, versus channel depth in microfabricated membranes.
Figure 13B:
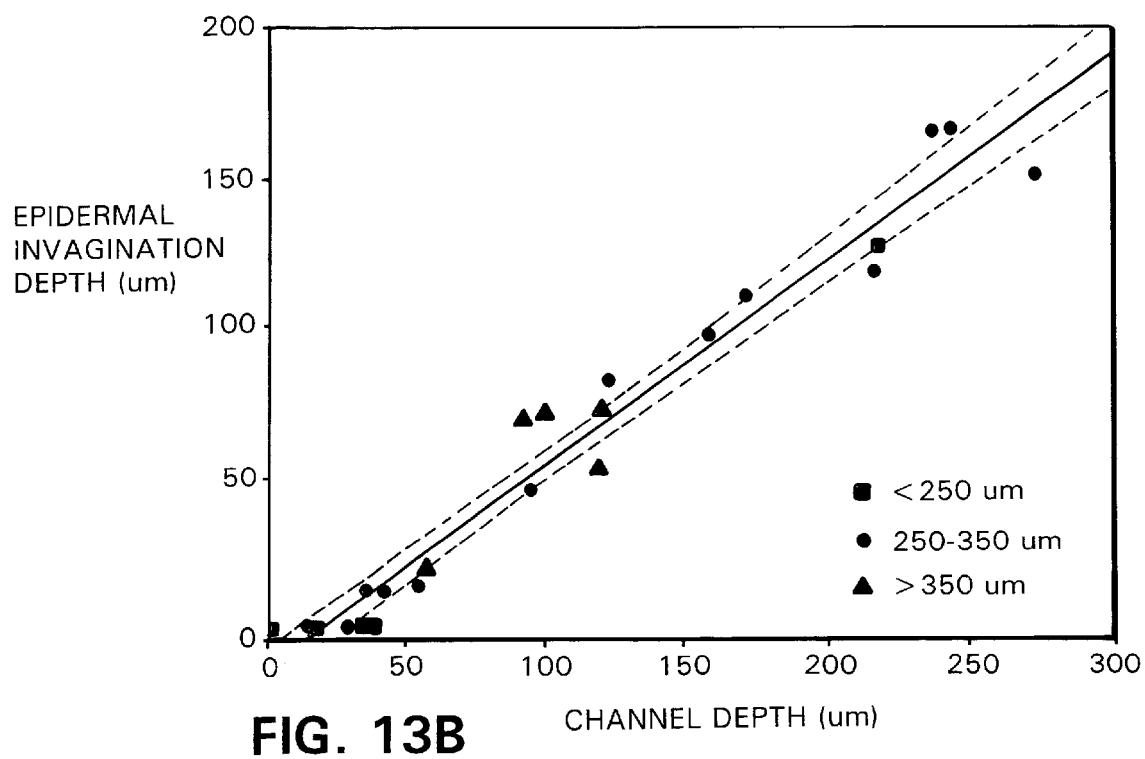

Morphometric analysis of the epidermal layer on the microfabricated membrane was conducted and measured as shown in FIG. 12. The schematic diagram of FIG. 12 shows the parameters used to measure the channel width (CW), channel depth (CD), epidermal thickness (ET), and epidermal invagination depth (EI) in each channel of the membrane. The graph in FIG. 13a illustrates the change in epidermal thickness versus channel depth, while the graph in FIG. 13b shows the epidermal invagination depth versus channel depth for each channel. For linear regression lines, $r^2=0.900$ (FIG. 13a) and 0.961 (FIG. 13b). The geometric shapes (squares, +, triangle) denote the different ranges of channel widths. Dashed lines are the 95% confidence levels for the linear regression lines. As shown in the graphs, the best fit for both of these linear relationships was for those channels whose widths were between 250 and 350 $\mu$m.

Uses

Microfabricated basal lamina analogs will have numerous applications in the emerging commercial field of tissue engineering, which seeks to create substitutes for a wide variety of human organs and tissues, many of which have basement membranes. For tissue engineered products which are assembled ex vivo, microfabricated basal laminae will allow for precise control of the three-dimensional organization of different types of cells as well as connective tissue layers. In the much the same way as naturally occurring basal laminae, microfabricated basal lamina analogs can be designed to control cell polarity, influence cell metabolism, act as a highly selective filter, induce cell differentiation, serve as specific highways for cell migration, and function as a selective barrier to the movement of cells. Thus, microfabricated basal lamina analogs will have an important role in the function as well as fabrication of complex tissues and tissue substitutes.

Cell differentiation can be controlled by topography by creating specific designs that mimic certain biological structures. For example, the test membranes with channels described herein demonstrate that the stratification of the epidermis is influenced by the depth of the channel, the deeper the channel the more stratified the cell layers. Thus, cell differentiation and/or proliferation can be influenced by controlling the topographical microenvironment of the cells.

As another example, a basal lamina microfabricated as a narrow tube or circular pocket with a closed bottom can be used to mimic the structure of a hair follicle. Such tubes or pockets can be made by laser etching a series of pockets of the desired size into the master plate, and then applying a conforming material that conforms to the walls of, but does not fill, the pocket. The tubes or circular pockets in the resulting microfabricated membrane are seeded with dermal papilla cells in the bottom and the rest of the tube is seeded with keratinocytes. This crowded tubular configuration of keratinocytes is what occurs in a naturally occurring hair follicle and may be the critical arrangement of keratinocytes that programs them to differentiate into and start growing as a hair. In this way, the arrangement of the keratinocytes within this tubular analog of the basal lamina influences cell metabolism, cell polarity, cell migration, and cell differentiation.

Another possibility is to make analogs of the basal lamina whose topography mimics the structures that occur during normal embryogenesis, morphogenesis, and organogenesis. These mimics could be seeded with cells, for example, cells grown from embryonic stem cells that have the capacity to differentiate into numerous different cell types, or they can be seeded with one or more differentiated cell types that occur during development. In this way, the basal analogs would position the cells into the correct places, thus facilitating the establishment of correct spatial gradients of growth factors and morphogens, that resume the development process and allow these analogs to proceed with morphogenesis or organogenesis.

One example of the use and advantages of microfabricated basal lamina analogs in tissue engineering is the fabrication of skin substitutes described herein. All of the current skin substitutes have a flat, thus unnatural, interface between the epidermal and dermal layers. By using a microfabricated basal lamina analog, a skin substitute was created with a complex interdigitating interface between the epidermal and dermal layers. This interdigitating interface has several advantages.

First, the mechanical strength bonding the epidermal and dermal layers together is significantly increased compared to a flat interface. This mechanical strength can be measured using known devices and techniques. For example, the mechanical strength of the composite materials could be tested by subjecting the materials to different shear stresses or by applying varying amounts of a vacuum in a blistering device and determining what force of vacuum is required to make these materials separate or blister. Thus, skin substitutes with a microfabricated basal lamina analog can be made which are more resistant to shear forces, a problem in external wound beds which often leads to graft failure.

Second, the interdigitating interface between epidermal and dermal layers facilitates improved mass transport between layers. Mass transport of nutrients, waste products, and growth factors to and from the epidermal layer is critical to the successful engraftment of any skin substitute. This process is significantly enhanced in skin substitutes containing microfabricated basal lamina analogs because of the greatly increased surface area, and the varying depths to which the basal lamina "reaches into" the underlying dermal layer.

Third, the outward appearance or cosmesis of a skin substitute can be precisely controlled using a microfabricated basal lamina analog. Present skin substitutes have an unnatural appearance due in part to the flat interface between the epidermal and dermal layers. By using a microfabricated basal lamina analog, it will be possible to design more natural and cosmetically appealing skin substitutes which have fine lines, wrinkles, and pore structures characteristic of native skin. Such properties are important to burn patients as well as other patients who receive skin substitutes for the treatment of ulcers or undergoing cosmetic/reconstructive surgery.

Fourth, microfabricated basal lamina analogs have applications in the fabrication of adnexal structures of the skin such as hair and sweat glands. Adnexal structures are characterized by deep invaginations of the epidermis into the dermis and are a complex interaction between cells of the epidermis and cells of the dermis. At the interface of these two layers is a basement membrane with a complex three-dimensional topography. Microfabricated basal lamina analogs that control the organization and interactions of epidermal and dermal cells are useful for the fabrication of these structures.

In addition, microfabricated basal lamina analogs and other microfabricated membranes can be used to introduce engineered cells into a patient, e.g., to include cells that produce polypeptides (e.g., heterologous polypeptides that the cells do not normally produce, or autologous polypeptides that the cells do produce, but not in such large amounts) such as growth factors (epidermal growth factor, fibroblast growth factor, platelet-derived growth factor, transforming growth factors, and the like), wound healing factors, hormones, or other proteins. In other applications, the cells in the new tissue analogs can be used for gene therapy to secrete polypeptides that the patient does not normally produce because of a defect, e.g., hormones and blood coagulation factors.

The skin and other tissues are an attractive target for applications in gene therapy because, for example, the keratinocytes of the epidermis can be easily cultured, genetically modified, assembled as part of a skin graft, and easily transplanted to a patient. Gene modified skin grafts can be used for the systemic delivery of therapeutic proteins (e.g., insulin), or for the local delivery of growth factors for wound healing (e.g., PDGF). Regardless of the application, the use of a microfabricated basal lamina analog would help to maximize the mass transport of the therapeutic protein from the skin graft, as well as to maximize the number of genetically modified keratinocytes per surface area of the graft, thus reducing the size of the needed skin graft.

The insertion of desired genes or other nucleic acid constructs into cells seeded onto the new microfabricated membranes or into the new tissue analogs or substitutes can be accomplished using routine genetic and recombinant engineering techniques, e.g., as described in Ausubel et al., eds., 1989, Current Protocols in Molecular Biology, Green Publishing Associates, Inc. and John Wiley & Sons, Inc., New York.

The new tissue analogs and substitutes, such as skin substitutes, can be tested in animal models to determine longevity and "take" of the material, vascularization, and maintenance of the defined three-dimensional topography of the microfabricated membranes. For example, the tissue substitutes can be implanted into athymic mice as described in Medalie et al., *J. Invest. Dermatol.*, 107:121–127, 122 (1996).

The new basal lamina can also be used to enhance mass transport in tissues or tissue analogs or equivalents other than skin. For example, the new membranes can be used to create engineered small intestines using a microfabricated membrane that mimics the topography of the intestinal mucosa.

The new microfabricated membranes can also be used in non-biological settings, e.g., in medical devices, water and other liquid filtration and/or purification systems, dialysis devices, cell culturing systems, and artificial organs such as bioartificial livers. In these devices, the three-dimensional topography of the microfabricated membranes is selected to achieve a high surface area, and to direct the flow of gases or liquids through tortuous pathways to increase the pathlength, and thus the time that the fluid remains in the device. The membranes can be located adjacent walls in the device or additional membranes to form stacks of membranes that allow flow between the membranes through the channels in the membranes, but not through the membranes. In other devices, such as size-exclusion filters, the membranes may be located to force fluids to pass through one or more membranes.

In various embodiments, the membranes can be manufactured of polymers that attract ions or charged proteins, e.g., for use in water purification, deionization, or desalination. The membranes can be made to have precise pores for filtration and dialysis. The membranes can include charged moieties or chelating agents to scavenge ions, heavy metals, or charged proteins or other molecules. Membranes with pores and charged moieties can be prepared to provide selectively permeable membranes.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A microfabricated membrane consisting of a sheet of conforming material that has a defined, three-dimensional topography comprising projections having a height of 10.0 to 1000 microns relative to the surface of the membrane.

2. A membrane of claim 1, wherein the three-dimensional topography further comprises invaginations having a depth of 10.0 to 1000 microns, relative to the surface of the membrane.

3. A membrane of claim 1, wherein the conforming material comprises gelatin.

4. A membrane of claim 1, wherein the conforming material comprises collagen.

5. A membrane of claim 1, wherein the conforming material comprises a polyurethane, a polylactic acid, TEFLON®, polystyrene, an epoxy resin, a methacrylate, a polycarbonate, a silicone, a non-collagenous protein, or a polysaccharide.

6. A membrane of claim 1, wherein the sheet of material is from 1 to 500 microns thick.

7. A basal lamina analog comprising a microfabricated membrane of claim 1, wherein the membrane is 1 to 50 microns thick, and the three-dimensional topography mimics a three-dimensional topography of a natural basal lamina.

8. An analog of claim 7, wherein the conforming material comprises gelatin.

9. An analog of claim 7, wherein the conforming material comprises collagen.

10. An analog of claim 7, wherein the membrane is 1 to 10 microns thick.

11. A membrane of claim 1, wherein the three-dimensional topography includes pores.

12. A membrane of claim 11, wherein the pores comprise a specified size or range of sizes.

13. A membrane of claim 1, wherein the sheet is permeable.

14. The membrane of claim 1, wherein the membrane is 10 to 50 microns thick.

15. A method of preparing a microfabricated membrane comprising a defined, three-dimensional topography, the method comprising creating a defined, three-dimensional master pattern;

microfabricating a master plate that corresponds to the defined, three-dimensional master pattern;

transferring the pattern or a negative of the pattern to a thin conforming material from the master plate; and allowing the conforming material to solidify to form the microfabricated membrane, wherein the membrane has a defined, three-dimensional topography that is substantially the same as the three-dimensional pattern of the master plate or a negative of the pattern of the master plate.

16. The method of claim 15, wherein the pattern is transferred from the master plate to the thin conforming material by applying the conforming material directly to the master plate, to produce a microfabricated membrane that has a defined, three-dimensional topography that is substantially the same as a negative of the three-dimensional pattern of the master plate.

17. The method of claim 15, wherein the pattern is transferred from the master plate to the thin conforming material by applying to the master plate a second conforming material in liquid or semi-solid form;

allowing the second conforming material to solidify, and removing the second conforming material from the master plate to form a negative replicate that comprises a negative of the master plate pattern;

applying the thin conforming material to the negative replicate; and allowing the thin conforming material to solidify to form the microfabricated membrane and removing the membrane from the negative replicate, wherein the membrane has a defined, three-dimensional topography that is substantially the same as the three-dimensional pattern of the master plate.

18. A method of claim 17, wherein the second conforming material comprises polydimethylsiloxane silicone (PDMS) elastomer.

19. A microfabricated membrane comprising a defined, three-dimensional topography comprising projections having a height of 1.0 to 1000 microns, prepared by the method of claim 15.

20. The membrane of claim 19, wherein the three-dimensional topography further comprises invaginations having a depth of 10.0 to 1000 microns.

21. A method of preparing a microfabricated tissue analog comprising a defined, three-dimensional surface topography, the method comprising creating a defined, three-dimensional master pattern;

microfabricating a master plate that corresponds to the defined, three-dimensional master pattern;

transferring the pattern or a negative of the pattern to a matrix material from the master plate; and allowing the matrix material to solidify to form the microfabricated tissue analog, wherein the analog has a defined, three-dimensional surface topography that is substantially the same as the three-dimensional pattern of the master plate or a negative of the pattern of the master plate.

22. A microfabricated matrix consisting of a three-dimensional conforming material that comprises at least one surface, wherein the surface has a defined, three-dimensional topography comprising projections having a height of 10.0 to 1000 microns, relative to the surface of the matrix.

23. The matrix of claim 22, wherein the three-dimensional topography further comprises invaginations having a depth of 10.0 to 1000 microns.

* * * * *